US011491276B2

(12) United States Patent
Wexler

(10) Patent No.: US 11,491,276 B2
(45) Date of Patent: Nov. 8, 2022

(54) PHARMACOTHERAPY OF NEUROSYSTEM DYSFUNCTIONS

(71) Applicant: Bruce E. Wexler, Hamden, CT (US)

(72) Inventor: Bruce E. Wexler, Hamden, CT (US)

( * ) Notice: Subject to any disclaimer, the term of this patent is extended or adjusted under 35 U.S.C. 154(b) by 0 days.

(21) Appl. No.: 17/687,263

(22) Filed: Mar. 4, 2022

(65) Prior Publication Data

US 2022/0288310 A1 Sep. 15, 2022

Related U.S. Application Data

(60) Provisional application No. 63/159,228, filed on Mar. 10, 2021.

(51) Int. Cl.
*A61M 5/172* (2006.01)

(52) U.S. Cl.
CPC ... *A61M 5/1723* (2013.01); *A61M 2205/3327* (2013.01); *A61M 2205/3334* (2013.01);
(Continued)

(58) Field of Classification Search
CPC .......... A61M 5/1723; A61M 2230/208; A61M 2205/581; A61M 2205/583;
(Continued)

(56) References Cited

U.S. PATENT DOCUMENTS 4,474,186 A * 10/1984 Ledley ................. A61B 5/4863
600/546
5,975,085 A 11/1999 Rise
(Continued)

FOREIGN PATENT DOCUMENTS

WO WO-2006021952 A2 * 3/2006 ............... A61B 5/11

OTHER PUBLICATIONS

Sar-El R, Sharon H, Lubianiker N, Hendler T, Raz G. Inducing a Functional-Pharmacological Coupling in the Human Brain to Achieve Improved Drug Effect. Front Neurosci. 2020;14:557874. Published Oct. 9, 2020. doi:10.3389/fnins.2020.557874.*
(Continued)

*Primary Examiner* — Theodore J Stigell
(74) *Attorney, Agent, or Firm* — Kilpatrick Townsend & Stockton LLP

(57) ABSTRACT

Release of a neurological drug in a targeted region of a subject's brain by a drug delivery system (DDS) is intentionally caused by the subject watching or interacting with an audio/video-based task on an electronic display. The DDS is calibrated to release the neurological drug based on a particular pH, lactate level, blood flow, temperature, magnetic field, specific molecules released by brain cells, or other physiological factors within the target region. The interactive task produces the physiological factors in the brain in specific areas of pathology for which the drug is prescribed, and limits drug delivery at areas unaffected by illness where it could disrupt normal function, causing problematic side effects and preventing dose levels optimal for target impact. Feedback from the interactive task and associated cognitive probes also can adapt the interactive task or suggest new pharmacologic agents as the degree or primary focus of brain pathology changes during the course of treatment.

15 Claims, 12 Drawing Sheets

(52) U.S. Cl.
CPC . *A61M 2205/505* (2013.01); *A61M 2205/581* (2013.01); *A61M 2205/583* (2013.01); *A61M 2210/0693* (2013.01); *A61M 2230/20* (2013.01); *A61M 2230/208* (2013.01); *A61M 2230/50* (2013.01)

(58) Field of Classification Search
CPC ...... A61M 2230/50; A61M 2205/3324; A61M 2205/3327; A61M 2205/3334; A61M 2205/505; A61M 2210/0693; A61B 5/026; A61B 5/377; A61B 5/383; A61B 5/4839
See application file for complete search history.

(56) References Cited

U.S. PATENT DOCUMENTS

| | | | | |
|---|---|---|---|---|
| 6,128,537 | A * | 10/2000 | Rise | A61M 5/14276 607/45 |
| 7,437,196 | B2 * | 10/2008 | Wyler | A61N 1/36067 607/45 |
| 7,729,773 | B2 * | 6/2010 | Sloan | A61N 1/36082 607/45 |
| 9,326,725 | B2 * | 5/2016 | Finkel | A61B 5/4827 |
| 2007/0179534 | A1 * | 8/2007 | Firlik | A61M 5/14276 604/503 |
| 2007/0287931 | A1 * | 12/2007 | Dilorenzo | A61K 31/5513 600/545 |
| 2009/0082829 | A1 * | 3/2009 | Panken | A61N 1/36139 607/45 |
| 2009/0105785 | A1 * | 4/2009 | Wei | A61N 1/36132 600/301 |
| 2010/0331807 | A1 | 12/2010 | Whitehurst et al. | |
| 2012/0088216 | A1 * | 4/2012 | Wexler | G09B 7/04 434/322 |
| 2019/0175040 | A1 * | 6/2019 | Arcot Desai | A61B 5/6868 |
| 2019/0329063 | A1 * | 10/2019 | Hendler | A61B 5/0263 |
| 2020/0016277 | A1 | 1/2020 | Broome et al. | |
| 2020/0023189 | A1 * | 1/2020 | Gribetz | A61N 1/36196 |
| 2020/0098276 | A1 | 3/2020 | Wexler | |

OTHER PUBLICATIONS

APA PsycNet, American Psychological Association, Accessed from internet on Feb. 18, 2021, 2 pages.
Ahmadi et al., Stimulus-Responsive Sequential Release Systems for Drug and Gene Delivery, Nano Today, vol. 34, Article 100914, Oct. 2020, 49 pages.
Barbera et al., A Wireless Miniscope for Deep Brain Imaging in Freely Moving Mice, Journal of Neuroscience Methods, vol. 323, May 2019, pp. 56-60.
Beland-Millar et al., Fluctuations of Extracellular Glucose and Lactate in the Mouse Primary Visual Cortex During Visual Stimulation, Behavioural Brain Research, vol. 344, May 15, 2018, pp. 91-102.
Bell et al., Neurocognitive Enhancement Therapy with Work Therapy: Effects on Neuropsychological Test Performance, Archives of General Psychiatry, vol. 58, No. 8, Aug. 2001, pp. 763-768.
Chandrasekaran et al., DNA Nanocages, Chemistry of Materials, vol. 28, Jul. 18, 2016, pp. 5569-5581.
Chong et al., Global Economic Burden of Schizophrenia: A Systematic Review, Neuropsychiatric Disease and Treatment, vol. 12, Feb. 16, 2016, pp. 357-373.
Cools et al., Striatal Dopamine Predicts Outcome-Specific Reversal Learning and its Sensitivity to Dopaminergic Drug Administration, Journal of Neuroscience, vol. 29, No. 5, Feb. 4, 2009, pp. 1538-1543.
Cremillieux et al., Online Quantification of Lactate Concentration in Microdialysate During Cerebral Activation Using 1H-MRS and Sensitive NMR Microcoil, Frontiers in Cellular Neuroscience, vol. 13, No. 89, Mar. 19, 2019, 8 pages.

Dinh et al., Characteristics of fMRI Responses to Visual Stimulation in Anesthetized vs. Awake Mice, NeuroImage, vol. 226, Article 117542, Available Online at: https://www.biorxiv.org/content/10.1101/2020.08.17.253500v1, Aug. 17, 2020, 42 pages.
Donegan et al., Amygdala Hyperreactivity in Borderline Personality Disorder: Implications for Emotional Dysregulation, Biological Psychiatry, vol. 54, No. 11, Dec. 1, 2003, pp. 1284-1293.
Farde et al., Central D2-Dopamine Receptor Occupancy in Schizophrenic Patients Treated with Antipsychotic Drugs, Archives of General Psychiatry, vol. 45, No. 1, Jan. 1988, pp. 71-76.
Feng et al., Polyelectrolyte Multilayer Functionalized Mesoporous Silica Nanoparticles for pH-Responsive Drug Delivery: Layer Thickness-Dependent Release Profiles and Biocompatibility, Journal of Materials Chemistry B, vol. 1, Sep. 20, 2013, pp. 5886-5898.
Fuzik et al., Integration of Electrophysiological Recordings with Single-Cell RNA-Seq Data Identifies Neuronal Subtypes, Nature Biotechnology, vol. 34, No. 2, Feb. 2016, pp. 175-183.
Gertz et al., Time-Dependent Increase in the Network Response to the Stimulation of Neuronal Cell Cultures on Micro-Electrode Arrays, Journal of Visualized Experiments, vol. 123, Article 55726, May 2017, pp. 1-16.
Grace, Dysregulation of the Dopamine System in the Pathophysiology of Schizophrenia and Depression, Nature Reviews Neuroscience, vol. 17, No. 8, Aug. 2016, pp. 524-532.
Hamilton et al., Time-Dependent Increase in Network Response to Stimulation, PLOS One, Available Online at DOI: 10.1371/journal.pone.0142399, Nov. 6, 2015, 15 pages.
Iturrioz-Rodriguez, Controlled Drug Delivery Systems for Cancer Based on Mesoporous Silica Nanoparticles, International Journal of Nanomedicine, vol. 14, May 8, 2019, pp. 3389-3401.
Kaar et al., Antipsychotics: Mechanisms Underlying Clinical Response and Side-Effects and Novel Treatment Approaches Based on Pathophysiology, Neuropharmacology, vol. 172, Article 107704, Aug. 1, 2020, 19 pages.
Kesby et al., Dopamine, Psychosis and Schizophrenia: The Widening Gap Between Basic and Clinical Neuroscience, Translational Psychiatry, vol. 8, No. 30, Dec. 2018, 12 pages.
Larsen et al., Activity-Dependent Astrocyte Swelling is Mediated By pH-Regulating Mechanisms, Glia., vol. 65, No. 10, Oct. 2017, pp. 1668-1681.
Li et al., Universal pH-Responsive and Metal-Ion-Free Self-Assembly of DNA Nanostructures, Angewandte Chemie, vol. 130, Jun. 2018, pp. 7008-7011.
Maghsoudi et al., Burgeoning Polymer Nano Blends for Improved Controlled Drug Release: A Review, International Journal of Nanomedicine, vol. 15, Jun. 19, 2020, pp. 4363-4392.
Magnotta et al., Detecting Activity-Evoked pH Changes in Human Brain, Proceedings of the National Academy of Sciences of the United States of America, vol. 109, No. 21, May 22, 2012, pp. 8270-8273.
Mitlohner et al., Dopamine Receptor Activation Modulates the Integrity of the Perisynaptic Extracellular Matrix at Excitatory Synapses, Cells, vol. 9, No. 260, Jan. 21, 2020, pp. 1-21.
Murray et al., Reinforcement and Reversal Learning in First-Episode Psychosis, Schizophrenia Bulletin, vol. 34, No. 5, Jul. 15, 2008, pp. 848-855.
Nordstrom et al., Central D2-Dopamine Receptor Occupancy in Relation to Antipsychotic Drug Effects: A DoubleBlind PET Study of Schizophrenic Patients, Biological Psychiatry, vol. 33, No. 4, Feb. 15, 1993, pp. 227-235.
Potenza et al., Gambling Urges in Pathological Gambling: A Functional Magnetic Resonance Imaging Study, Archives of General Psychiatry, vol. 60, Aug. 2003, pp. 828-836.
Prichard et al., Lactate Rise Detected by 1H NMR in Human Visual Cortex During Physiologic Stimulation, Proceedings of the National Academy of Sciences of the United States of America, vol. 88, No. 13, Jul. 1, 1991, pp. 5829-5831.
Hajebi et al., Stimulus-Responsive Polymeric Nanogels as Smart Drug Delivery Systems, Acta Biomaterialia, vol. 92, Jul. 1, 2019, pp. 1-18.
Schlagenhauf et al., Striatal Dysfunction During Reversal Learning in Unmedicated Schizophrenia Patients, NeuroImage, vol. 89, No. 100, Apr. 1, 2014, pp. 171-180.

(56) References Cited

OTHER PUBLICATIONS

Sugimoto et al., Preparation of Dual-Stimuli-Responsive Liposomes Using Methacrylate-based Copolymers with pH and Temperature Sensitivities for Precisely Controlled Release, Colloids and Surfaces B: Biointerfaces, vol. 155, Jul. 1, 2017, pp. 449-458.

Tam et al., Penetrating the Blood-Brain Barrier by Self-Assembled 3D DNA Nanocages as Drug Delivery Vehicles for Brain Cancer Therapy, ACS Applied Materials & Interfaces, vol. 12, No. 26, Jul. 1, 2020, pp. 28928-28940.

Theparambil et al., Astrocytes Regulate Brain Extracellular pH via a Neuronal Activity-Dependent Bicarbonate Shuttle, Nature Communications, vol. 11, Article 5073, Oct. 8, 2020, 15 pages.

Villers-Sidani et al., Recovery of Functional and Structural Age-Related Changes in the Rat Primary Auditory Cortex with Operant Training, Proceedings of the National Academy of Sciences of the United States of America (PNAS), vol. 107, No. 31, Aug. 3, 2010, pp. 13900-13905.

Wang et al., A SERS Optophysiological Probe for the Real-Time Mapping and Simultaneous Determination of the Carbonate Concentration and pH Value in a Live Mouse Brain, Angewandte Chemie, vol. 131, No. 16, Feb. 2019, pp. 5310-5314.

Wexler et al., Cognitive Remediation and Vocational Rehabilitation for Schizophrenia, Schizophrenia Bulletin, vol. 31, No. 4, Aug. 3, 2005, pp. 931-941.

Wexler et al., Functional Magnetic Resonance Imaging of Cocaine Craving, The American Journal of Psychiatry, vol. 158, No. 1, Jan. 2001, pp. 86-95.

Wexler et al., Normal Neurocognitive Performance After Extended Practice in Patients with Schizophrenia, Schizophrenia Research, vol. 26, Issues 2-3, Aug. 29, 1997, pp. 173-180.

Wexler et al., Preliminary Evidence of Improved Verbal Working Memory Performance and Normalization of Task-Related Frontal Lobe Activation in Schizophrenia Following Cognitive Exercises, The American Journal of Psychiatry, vol. 157, No. 10, Oct. 2000, pp. 1694-1697.

Yilmaz et al., Antipsychotics, Dopamine D2 Receptor Occupancy and Clinical Improvement in Schizophrenia: A Meta-Analysis, Schizophrenia Research, vol. 140, No. 1-3, Sep. 2012, pp. 214-220.

Application No. PCT/US2022/019003, International Search Report and Written Opinion, dated Jul. 19, 2022, 6 pages.

\* cited by examiner ly relate to
PHARMACOTHERAPY OF NEUROSYSTEM DYSFUNCTIONS

CROSS-REFERENCES TO RELATED APPLICATIONS

This application claims the benefit of U.S. Provisional Application No. 63/159,228, filed Mar. 10, 2021, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

Embodiments of the present invention generally relate to controlling the release of a drug delivery system (DDS) for neurological drugs using a subject's willful cognitive or motor stimulation to alter chemistry, etc. in a targeted neurofunctional system of the subject's brain.

2. Description of the Related Art

Schizophrenia and depression are chronic debilitating central nervous system (CNS) disorders affecting millions of people worldwide. With onset of schizophrenia in the second and third decades and lifelong persistence, the effects on individuals, families, and collective societal costs of medical care and lost productivity are estimated at $60 billion annually in the United States alone.

Currently available pharmacotherapy (drugs) are partially effective, but use and effectiveness are significantly limited by side effects of the drugs. Side effects are a major reason life expectancy is reduced by 15 years in people with schizophrenia, and they also negatively impact quality of life for people suffering from schizophrenia. Furthermore, while some studies indicate that higher than customary doses may increase symptom reduction, the associated side effects make such doses unsafe and unacceptable for most subjects.

Side effects not only limit maximum dosing, they may prevent candidate drugs from being approved in the first place. For example, they may create safety problems leading to failure to gain U.S. Food and Drug Administration (FDA) clearance. Or they may present limits on dosage to subtherapeutic levels. That is, side effects can render such drugs unsafe or ineffective. Of candidate drugs developed in preclinical studies for CNS disorders, 93% fail clinical trials.

A major cause of all these limitations is the fact that medications are delivered through the blood throughout the entire brain rather than specifically where needed for therapeutic action. Therefore, the drug chemicals contact more than the region for which they are intended. Or, the drug chemicals are not dosed in sufficient amounts to the targeted region.

Essentially, all currently used medications for schizophrenia work through blockade of dopamine $D_2$ receptors in the substantia nigra. The substantia nigra is a basal ganglia structure in the midbrain that services rewards, among other things.

FIGS. 1A-1B are positron emission tomography (PET) images showing blockade of the $D_2$ receptors in the substantia nigra by an antipsychotic drug of the prior art. In each figure, what are shown are levels 102A-B of uptake of a radioactive label in $D_2$ receptors in substantia nigra of a subject with schizophrenia. FIG. 1A shows a level 102A of uptake before treatment, and FIG. 1B shows level 102B, which corresponds to a reduction of uptake after treatment with antipsychotic medication that occupies the receptors and prevents uptake of dopamine (i.e., dopamine blockade).

The reduction in uptake, caused by the drug's blockade of $D_2$ receptors in the associative subdivision of the substantia nigra, is the main therapeutic benefit of the antipsychotic drug. Yet there are other subdivisions of the substantia nigra that are also affected by the drug.

There are three functionally distinct subdivisions of the substantia nigra: motor (MSN), associative (ASN) and reward/motivation (RMSN).

Midbrain dopamine neurons are the source of dopamine projections to the striatum in primates, and these structures are shared with other animals such as rodents. In primates, the limbic system originates in the dorsal tier of the substantia nigra. In the rodent, the limbic system originates in ventral tegmental area, which sits medially to the substantia nigra. The midbrain projections to the associative striatum and sensorimotor striatum follow a dorsomedial-to-ventrolateral topology.

When a drug is administered, it travels into all of the regions above. Side effects come from at least two sources: 1) $D_2$ receptors are located in many parts of the brain unrelated to the site of required therapeutic action, including parts of the substantia nigra, and unrelated to the function of these other areas impacted by the drugs; and 2) available $D_2$ receptor blocking medications also effect receptors for other neuromodulators throughout the brain, creating additional unwanted side effects through these effects.

A side effect from schizophrenia medications includes abnormal movements (referred to as extrapyramidal effects), which affect up to 35% of subjects depending on the particular medication and include stiffness, Parkinson-like bradykinesia and rigidity, tremors in the hands, and involuntary repetitive movements of the mouth, head or arms. The repetitive movements may persist even after the medications are stopped. The literature describes this after effect as tardive dyskinesia. It is caused by $D_2$ blockade in the division of the substantia nigra related to motor control (MSN) which is adjacent to the area of therapeutic action in the ASN.

Other side effects include endocrine side effects, which occur in 20-40% of subjects and are related to increased prolactin levels caused by $D_2$ blockade in the pituitary gland. Side effect symptoms include enlarged breasts and impaired sexual function in men and painful breasts and lactation in women.

Weight gain and metabolic side effects are a major factor in reduced longevity. On these medications, it is not uncommon for subjects to gain 50 pounds or more. This results in part from $D_2$ blockade in another division of the substantia nigra associated with reward and appetitive behaviors, a region also adjacent to the sites of therapeutic action in the ASN. Weight gain also results from the impact of antipsychotic drugs on histamine Hi and serotonin 5-HT2C receptors that are not thought to be associated with clinical benefit.

The side effects may also involve secondary negative symptoms of dysphoria and a complex of subjective experiences of "low subjective well-being" including decreased cognitive function, emotional regulation, physical functioning and social integration are associated with $D_2$ blockade in the temporal lobe and insula as well as parts of the substantia nigra related to reward and motivation.

Sedation is one of the most problematic side effects with regard to quality of life and is also linked to histamine Hi antagonism.

Cognitive impairment, dry eyes and mouth, urinary retention and constipation all result from anticholinergic effects from blockade of muscarinic receptors.

With this backdrop to side effects of neurological drugs and their physiological causes, it is apparent that there is a need in the art for more targeted treatments in the brain for schizophrenia and other central nervous system disorders.

BRIEF SUMMARY

Generally, a neurological drug is attached to drug delivery system (DDS) that releases the drug when in the presence of local physiological factors in a subject's brain. The local physiological factors are deliberately, intentionally created by the subject when he or she performs a predetermined task or challenge. The task or challenge is presented through audio, or a video display, or in an immersive virtual reality (VR) environment. It may include a video game, puzzle, matching or contrast problem, or other challenge. The local physiological factors in the brain may include change in pH, lactate levels, blood flow, temperature, change in the local magnetic field, and other such factors. Although slight, these factors are measurably affected by the subject performing the task and are used to trigger the DDS's release of the drug.

Before, during, or after treatment, a computer monitoring and intervention system can continuously and non-invasively assesses neurosystem dysfunction in individual subjects in order to identify a neurosystem dysfunction and pharmacotherapy targets for each individual. In addition, the intervention system can continue to assess neurosystem function throughout the course of treatment in order to modify the pharmacotherapy target, the release set-point of the DDS for greater sensitivity or specificity of neural system targeting, and the pharmacotherapy agent. Drugs delivered by the DDS sensitive to physiological changes associated with local neural system activity may itself be in a sustained-release structure to enable continued localized pharmacologic effects after cessation of the extrinsic neural-activation designed to produce localized drug release.

Some embodiments of the invention are related to a method of activating neurological pharmacotherapy through targeting activation tasks by a subject, the method including administering a drug delivery system (DDS) to a subject, the DDS carrying a neurological drug, the drug delivery system configured to release the neurological drug when encountering a predetermined pH, lactate level, blood flow, temperature, magnetic field, or specific molecules released by brain cells, presenting a targeting activation task to the subject, wherein the targeting activation task is selected in order to change a pH, lactate level, blood flow, temperature, magnetic field, or a concentration of the specific molecules in physical locations of a predetermined neurofunctional system of a brain of the subject, and releasing, from the DDS, the neurological drug at the physical locations of the neurofunctional system within the brain based on the changed pH, lactate level, blood flow, temperature, magnetic field, or concentration of the specific molecules caused by the targeting activation task.

The targeting activation function can be a sensory-motor brain activation task and the presenting of the targeting activation task can include instructing the subject to move an appendage. The movement can include periodic movement in a rhythm. The instructing can include starting or stopping the movement.

The targeting activation function can be a neurocognitive task and the presenting of the targeting activation task can include displaying, on a video display, an interactive game or challenge, and receiving interactive inputs from the subject and updating the video display in response to the interactive inputs. The video display can include virtual reality goggles.

The presenting of the targeting activation task can include playing, on a speaker, an audible game or challenge, and receiving interactive inputs from the subject and updating the audible game or challenge in response to the interactive inputs.

The method can include measuring the releasing through a sensor, and adjusting a length or intensity of the targeting activation task in response to a value obtained from the measuring. It can include adapting the targeting activation task based on the changed pH, lactate level, blood flow, temperature, magnetic field, or concentration of the specific molecules in the brain of the subject, and stopping the targeting activation task when a predetermined dose of the neurological drug is estimated to be released.

The method can include waiting a predetermined time for the drug delivery system to cross the blood brain barrier of the subject before presenting the targeting activation task.

The drug delivery system can be selected from the group consisting of a deoxyribonucleic acid (DNA) nanocage, cellular delivery system, a microelectromechanical (MEMs)-based device, a polymer matrix, and a gene delivery system. The releasing of the drug can include unbinding from or exposing an active region of the drug.

The subject can be a human or other mammal. The human can suffer from a central nervous system disease. The central nervous system disease can be a psychiatric disease.

DETAILED DESCRIPTION

Figure 1B:
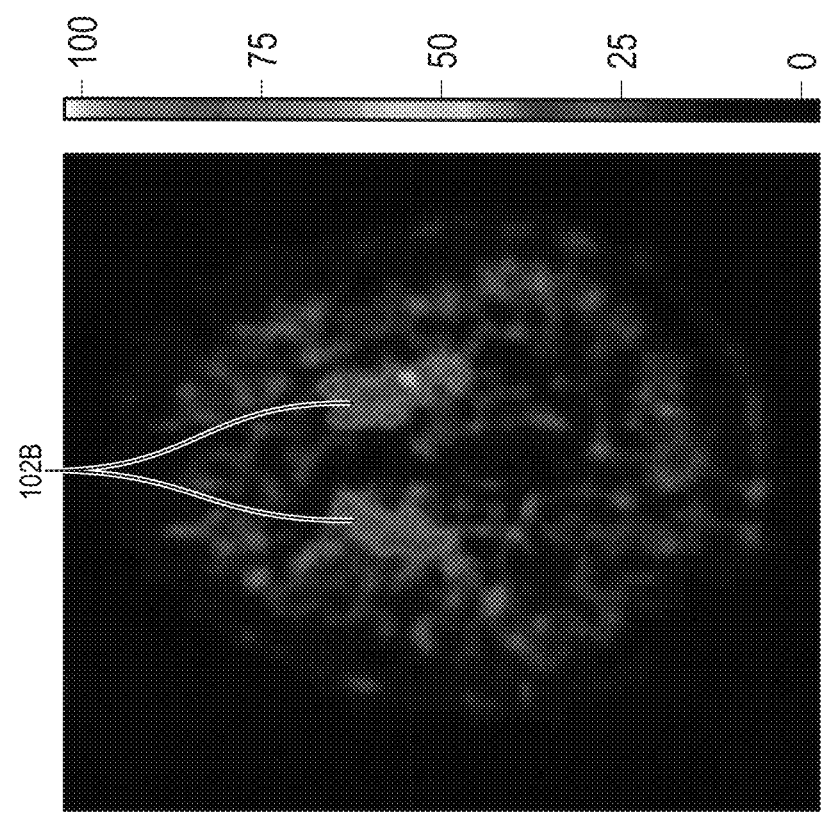
FIG. 1B is a PET image of the subject of FIG. 1A after treatment with the antipsychotic medication.
Figure 1A:
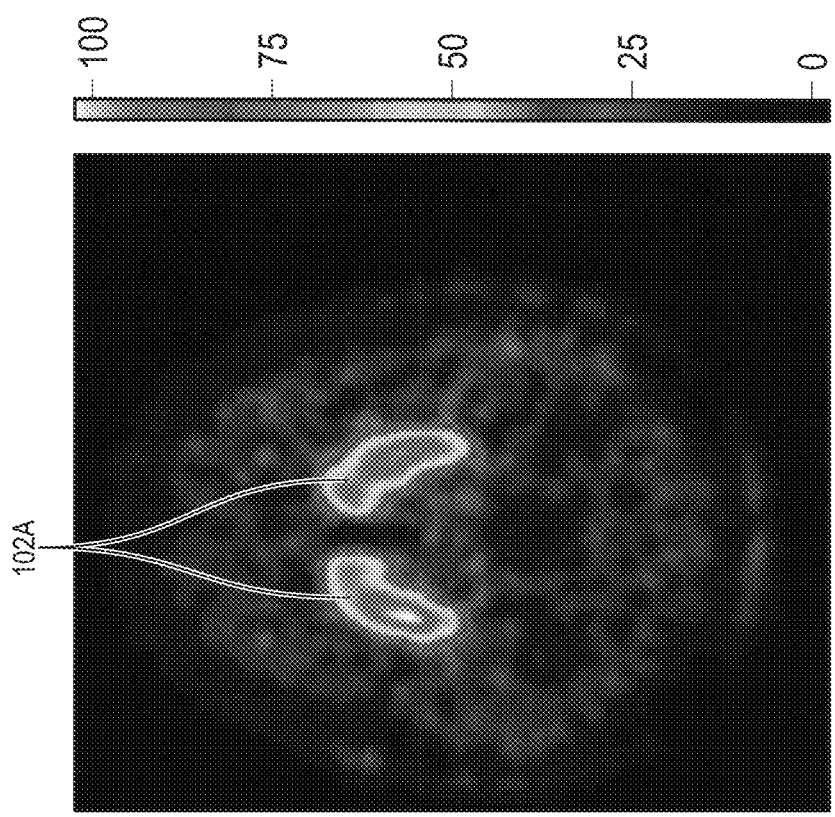
FIG. 1A is a positron emission tomography (PET) image of a subject with schizophrenia before treatment with an antipsychotic medication of the prior art.
Figure 2A:
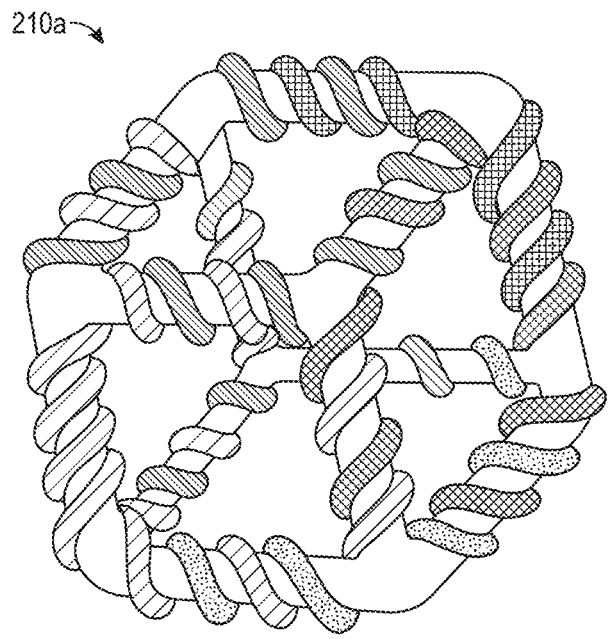
FIGS. 2A-2F illustrate deoxyribonucleic acid (DNA) nanocage drug carriers in accordance with an embodiment.
Figure 2B:
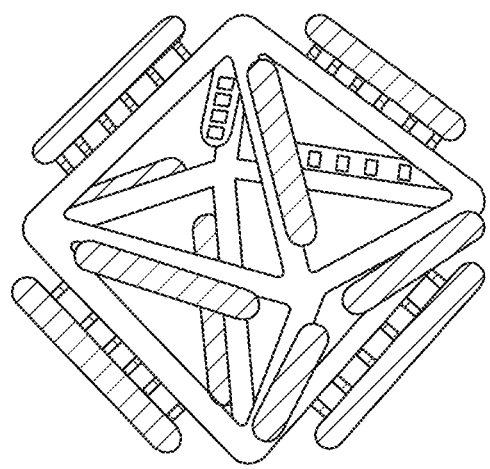
Figure 2C:
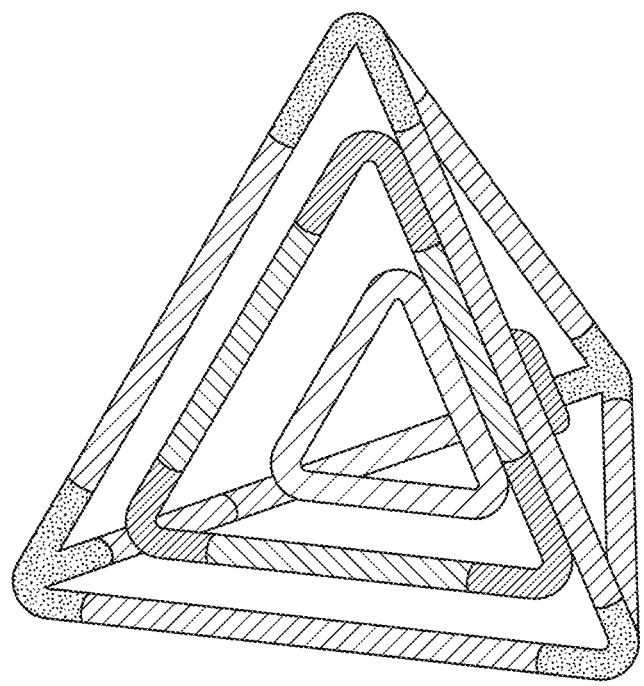
Figure 2D:
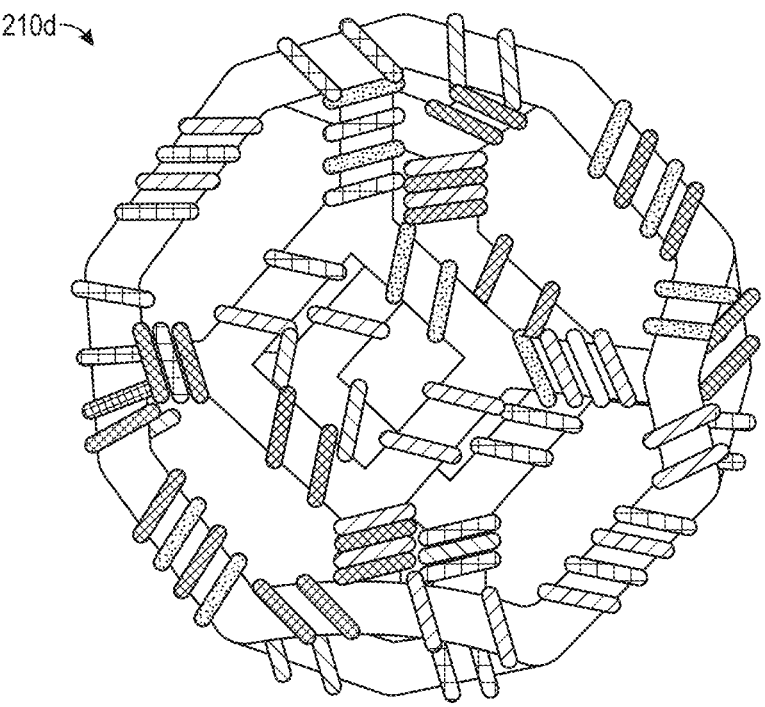
Figure 2E:
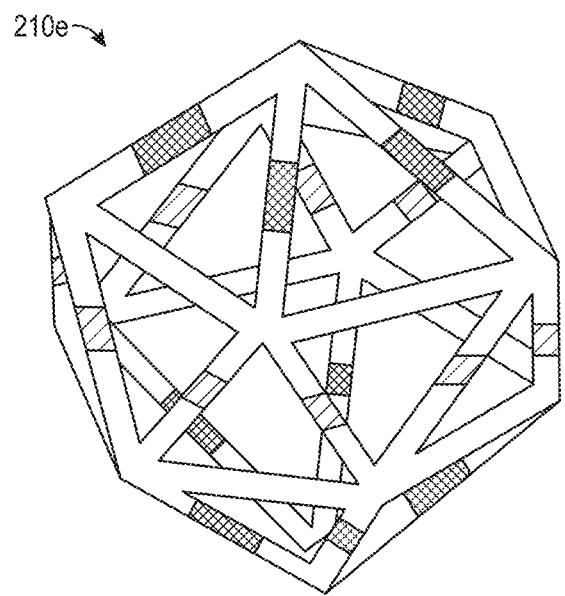
Figure 2F:
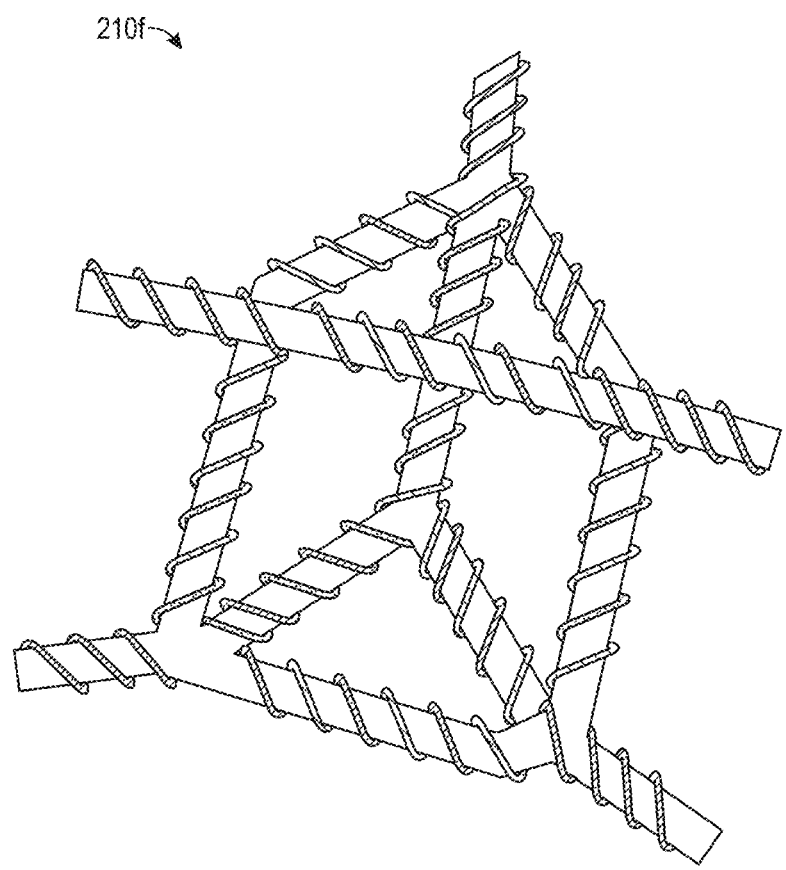
Figure 3A:
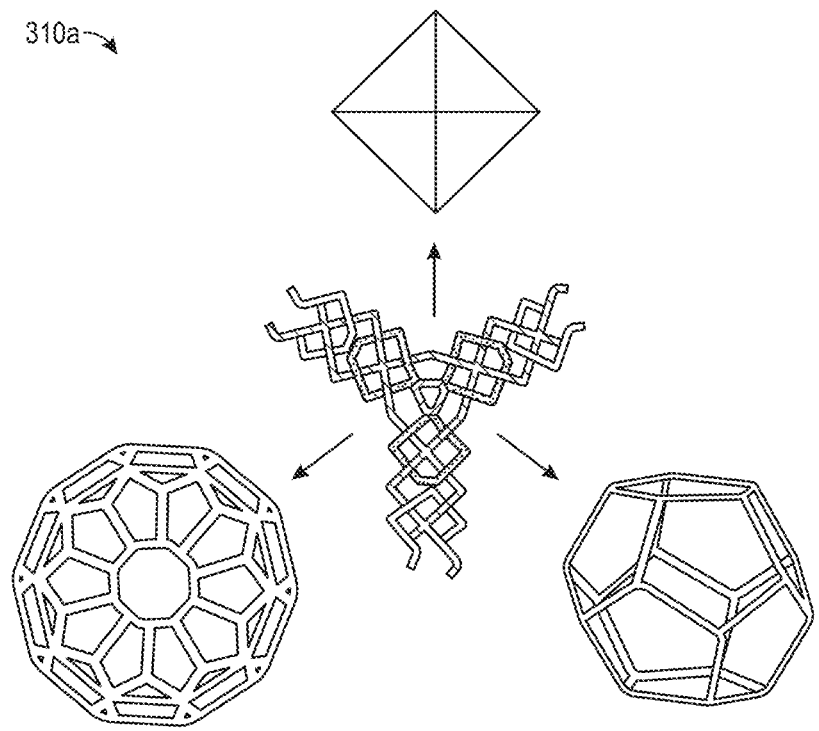
FIGS. 3A-3C illustrate additional deoxyribonucleic acid (DNA) nanocage drug carriers in accordance with an embodiment.
Figure 3B:
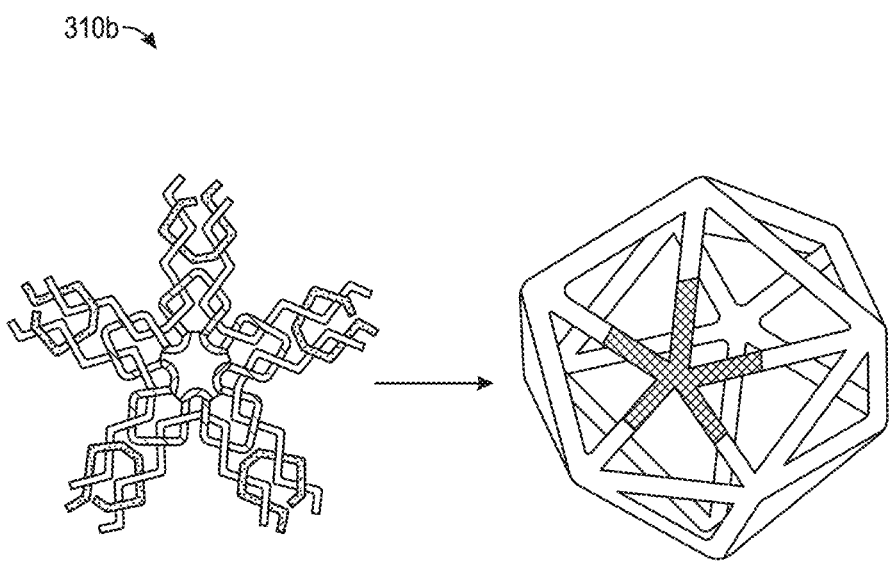
Figure 3C:
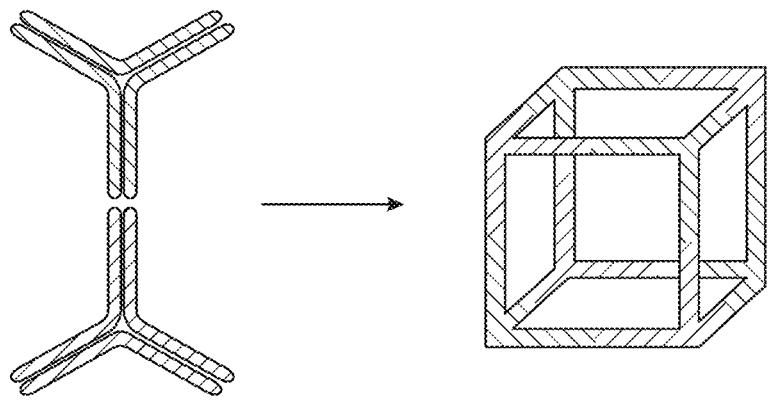
Figure 4:
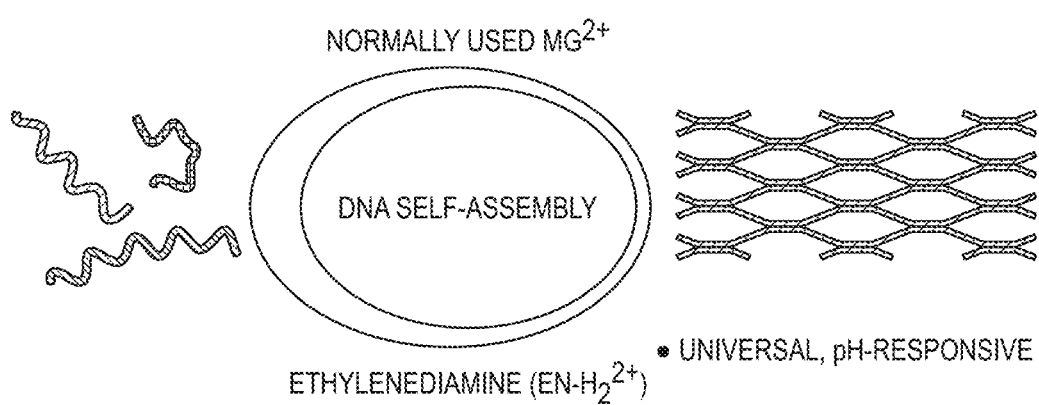
FIG. 4 illustrates a universal pH sensitive DNA nanocage drug delivery system in accordance with an embodiment.
Figure 4:
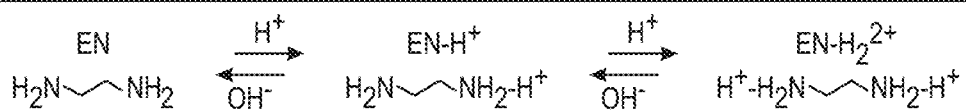

Many important targets for drug treatment are inside the body, and most pharmacologic agents are delivered to the desired site of action through the blood, either after ingestion or by being introduced intravenously. This creates a problem in that the blood circulates and carries the drug to all parts of the body, many or most of which are not sites of pathology. These other parts may be affected by the drug, creating side effects that limit drug net benefit, may present safety concerns preventing approval of the drug at all, and may limit the maximum dose of the drug to levels too low to impact the target pathology.

In order to address these problems, drug delivery systems have been developed that carry the drug through the blood in an inactive form and then respond to some feature at the location of pathology to activate the drug. For example, the drug may be transported in a "container" that becomes porous and releases the drug in response to physiological factors in the local environment of the targeted pathology. Or the drug may be biochemically bound to another molecule rendering it inactive but cleaves off in response to local factors. The local factors are typically associated with metabolic activity such as pH, blood flow, metabolic by-products, temperature, magnetic field, and/or other factors.

Drug delivery systems have been pioneered to deliver anti-cancer drugs. A cancer tumor itself has distinct metabolic features, such as higher temperatures, that are different from surrounding healthy tissues. Thus, a higher temperature of the tumor can trigger drug release. In some other instances, an external light is shone through the skin reaching internal body locations to trigger light sensitive mechanisms in the drug delivery system in order to release the drug.

A "drug delivery system" (DDS) includes an engineered system for administering a pharmaceutical compound to a subject, or as otherwise known in the art. The term includes macroscopic devices such patches and microneedles, and it also includes nanoscale particles (e.g., DNA nanocages), bacteria, viruses, or other microscopic carriers.

A microscopic "drug delivery system" (DDS) includes an engineered carrier made from liposomes, proliposomes, microspheres, gels, prodrugs, cyclodextrins, or other materials that can be attached to a drug compound and target a particular portion of the body, or as otherwise known in the art. Once at the target, the drug delivery system is configured to uncover, expose, or otherwise release the cargo drug in response to local factors such as pH, lactate levels, blood flow, temperature, a magnetic field, and/or other factors.

"Releasing" a cargo drug from a drug delivery system includes uncovering an entirety of or portion of, letting go of it, liberating, activating, or otherwise allowing the drug to perform its intended therapeutic function in the subject's body from a state when the drug delivery system prevented the drug from performing, or as otherwise known in the art. For example, a drug delivery system may encapsulate the drug then become porous and release the drug in response to physiological factors in the local environment of the targeted pathology. Or the drug may be biochemically bound to another molecule of the drug delivery system rendering it inactive but cleave off in response to local factors.

DDSs do not appear to have been used previously to treat psychiatric and other central nervous system (CNS) diseases, which together constitute a leading source of disease burden world-wide. Failure to apply this approach to disorders of the CNS, despite the wide need and strikingly limited effects of current treatments, may indicate the absence of methods to produce physiological or local triggers to activate drug at desired sites for drug impact. The brain is somewhat isolated fluidically from the rest of the body, and it is understandably well protected, sensitive, and difficult to probe with common surgical tools.

However, digitally provided neurotherapy exercises, presented through an audio/visual display, that increase neuronal activity and function in targeted neural systems compromised by illness can produce local physiological changes that sufficiently trigger DDS release of therapeutically active drugs. This enables highly-focused directed delivery of drugs to the specific dysfunctional neurosystems in individual subjects, increasing effectiveness and decreasing side-effects.

For example, they can allow selective delivery of a $D_2$ antagonist to the associative substantia nigra to maximize the benefit of the drug effects and minimize side effects.

This approach addresses multiple limitations that may have prevented enhanced drug treatment of psychiatric and other CNS disorders, such as the following.

Many psychiatric and CNS medications work by blocking or enhancing trans-synaptic neuronal signal transmission. This may be done, for example, by blocking access to a specific post-synaptic receptor, directly activating a post-synaptic receptor, or preventing breakdown of endogenously released neurotransmitters thereby increasing their concentration and impact on post-synaptic receptors. The problem is that the same individual neurotransmitters function throughout the brain. As a result, drugs delivered throughout the brain via blood flow impact the function of many neural functional systems and have many significant side effects.

Additionally, CNS dysfunctions in psychiatric and other illnesses are associated with alterations in multiple neurotransmitters and modulators. Although theories of action of the first medications for disorders like schizophrenia and depression focused on single neurotransmitter disorders, second and third generation medications—which have proved more effective—typically impact multiple neurotransmitters and modulators. This increases the potential for wider brain impact and associated side effects, especially when higher doses are attempted for partially or non-responsive subjects.

In addition, current clinical diagnostic categories include individuals with different brain pathology and different mixes of neurosystem dysfunctions. Brain imaging and genetic risk studies have established that individuals with the same diagnosis can have very different underlying brain dysfunctions, and subjects with different diagnoses can share specific underlying brain dysfunctions. For these reasons, it is increasingly recognized that in order to be more effective, treatments of CNS diseases should be individualized well beyond any guidance provided by diagnosis. Research theory and priority at the U.S. National Institutes of Health (NIH) have changed accordingly to focus on dimensions of function across diagnostic categories. However, practical devices or systems do not exist to translate this perspective into treatment for individual subjects.

A combined approach of using a drug delivery system in conjunction with the subject performing tasks to stimulate neurofunctional regions of his or her brain provides a concrete procedure to dramatically increase specificity of treatment of psychiatric and CNS disorders on two dimensions. First, it helps in the realm of targeted pharmacotherapy of specific disease-related brain functional systems rather than exposing the brain as a whole to drug effects. Second, it allows personalized treatment of neurosystems dysfunctions specific to each subject. That is, personalized audio-visual presentations can be rendered based on how the subject is diagnosed as well as how he or she is reacting in real-time.

The system can include a determination of specific disease-related brain functional systems in specific individuals. It can use a set of sensory detection and information processing probe tests to identify dysfunctions in each individual, and to monitor improvement or shifting dysfunctions through the course of treatment. Visual and auditory probes can be presented digitally and adapt rapidly to efficiently focus on and further specify dysfunction. In some instances olfactory, gustatory, or somatosensory probes are used.

The system can assist delivery of pharmacotherapy to specific disease-related brain functional systems. It can employ existing DDSs or modifications thereof that already have proven effective in providing targeted pharmacotherapy in cancer and other body disorders but have not previously been used for psychiatric or CNS disorders. It is also possible to develop de novo DDSs. Based on the set of dysfunctions identified, the system can create a custom targeting activation task, e.g., a set of visually presented digital cognitive games, to engage and induce increases in neuronal firing in the dysfunctional system. Local physiological changes related to the targeted local increases in neuronal firing, e.g., associated metabolic activity and energy consumption, trigger activation of the DDS.

FIGS. 2A-4 illustrate several DNA nanocage drug carrier drug delivery systems (DDSs) 210a, 210b, 210c, 210d, 210e, 210f, 310a, 310b, 310c, and 410 in accordance with an embodiment. There are several methods and materials with which to construct DDSs. As way of example, DNA nanocages provide highly versatile carriers that pass through the blood brain barrier and can be triggered to open and release drugs, or expose an active region of a drug, by a variety of local physiologically based ligands, biomolecules, changes in temperature, changes in lactate level, changes in blood flow, changes in magnetic field, or changes in pH.

The pH sensitive systems are of particular interest because they can be constructed with various set points for release adjusted by the chemical nature of hydrogen bonding groups on the nanocage. Alternative DDSs can be constructed with release set-points at different pH levels, using, for example, mesoporous silica nanoparticles. Applying different numbers of layers of poly(allyamine hydrochloride) and poly(styrene sulfonate) to mesoporous silica nanoparticles allows tuning of the pH sensitive release points. Additionally, as illustrated with DDS 410 in FIG. 4, ethylenediamine (EN) may be used for a pH-responsive nanocage.

In the exemplary embodiment, a DDS can carry an antipsychotic medication, e.g., haloperidol, through the blood stream throughout the body and brain in inactive form. The DDS releases the drug in active form in response to a trigger present at the site of desired therapeutic action.

Figure 5:
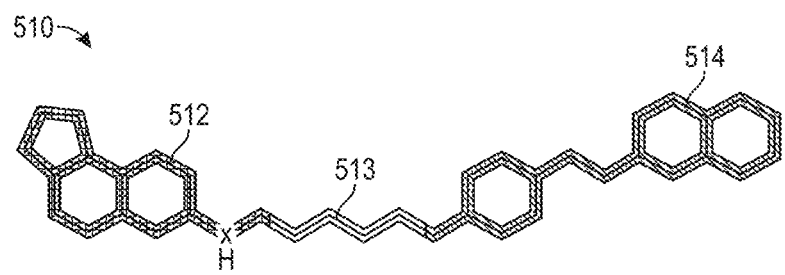
FIG. 5 illustrates a carrier prodrug drug delivery system in accordance with an embodiment.

FIG. 5 illustrates a carrier prodrug DDS 510 in accordance with an embodiment. The DDS 510 includes a neurological drug 512, a linker 513, and a carrier 514. With the carrier 514 linked to the neurological drug 512, the neurological drug 512 is inactive. But, the carrier 514 can be cleaved, e.g., by an enzyme or other biomolecule, from the neurological drug 512, thus activating the neurological drug 512.

While FIGS. 2A-5 describe DNA nanocages and carrier prodrugs, other examples of DDSs can include cellular delivery systems, microelectromechanical (MEMs)-based devices, polymer matrices, and gene delivery systems.

Figure 6:
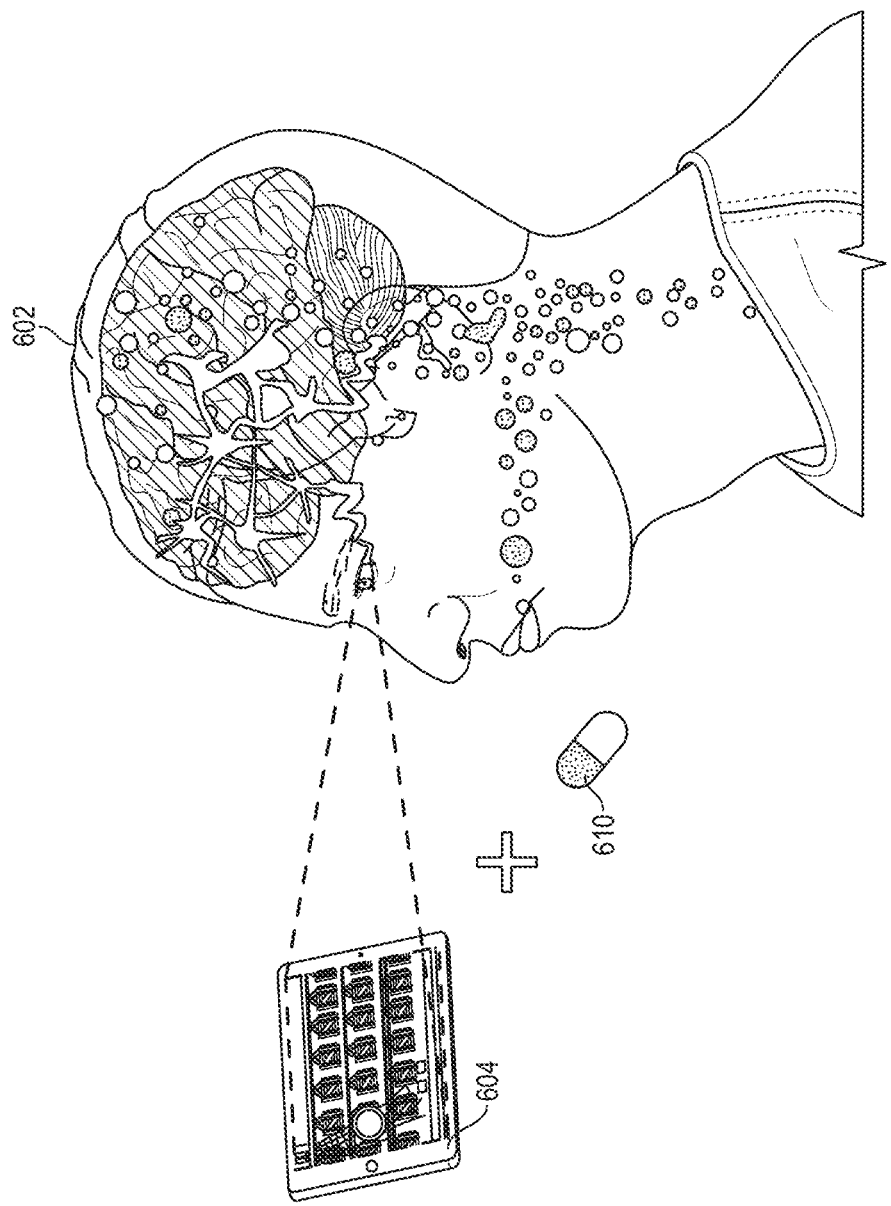
FIG. 6 illustrates a subject performing a digital neurotherapy exercise with a video display in accordance with an embodiment.

FIG. 6 illustrates a subject 602 performing a digital neurotherapy exercise with an audio/video (A/V) display in accordance with an embodiment. A targeting activation task 604 triggers drug release from a DDS 610 in a targeted neurofunctional system. For instance, the targeting activation task 604 can be a neurocognitive task or a sensory-motor brain activation task. A neurocognitive task can involve a display of an interactive game or cognitive challenge that the subject 602 interacts with. The display can update based on the interactions of the subject 602. In some instances, the display may be made by a computer or virtual reality goggles. Another example of a neurocognitive task can involve a speaker playing an audible game or cognitive challenge. The subject 602 can interact with the speaker to provide interactive inputs, which can then update the audible game or cognitive challenge. A sensory-motor brain activation task can involve instructing the subject 602 to move an appendage. The movement may involve a periodic movement in a rhythm, such as a periodic tapping of a hand to at an indicated frequency (e.g., once per second). The targeting activation task 604 can indicate to the subject 602 a starting and/or stopping of the movement. A predetermined time may be waited for the DDS 610 to cross a blood brain barrier of the subject 602 before the targeting activation task 604 is presented to the subject 602.

As an example, the associative subdivision of the substantia nigra ASN is strongly activated during tasks requiring behavioral flexibility. It may be particularly well suited for neurological drugs targeted with DDSs because the ASN is the only known common region required for goal-directed action that is sensitive to outcome devaluation and serial reversal learning in both animal and human studies. These functions are compromised in subjects with schizophrenia.

In the case of targeted delivery of $D_2$ antagonist drugs to treat schizophrenia, the targeting activation task 604 performed by the subject 602 can involve outcome devaluation and serial reversal tasks presented in a user interface (UI) application module in at least daily "drug activation sessions." Each drug activation session with the UI application can include 30 minutes of task performance, with task difficulty continuously adjusted based on monitoring of performance accuracy in order to maintain performance between a particular range, e.g., 75% and 90% accuracy. The particular range can be selected to ensure engagement and challenge of the ASN. One or more task parameters can be adjusted to individualize difficulty to maintain desired performance levels. These parameters can include, for example, degree of similarity of valued and devalued stimuli (e.g., two types of cookies vs cookie and apple), intrinsic appeal of the devalued stimulus vs the valued (e.g., ice cream vs an apple), duration of stimulus exposure and time between successive stimuli, percentage of reversed foils, frequency of reversing the learned associations or pairing of stimulus components, and provision of clues and strategy advice.

The UI application can include software instructions executed by a general purpose or other computer, the software stored in a volatile or non-volatile memory or loaded across a computer network. The software can include interactive elements such as those supported by Microsoft Windows, Apple macOS, Google Chrome, or other operating systems. They may be entirely browser based or be loaded as a program on the local computer.

Example Work Flow: Subject and Doctor Experience

An example of a workflow for a doctor and subject is described herein. First, a doctor can perform a clinical evaluation, assign a diagnosis, and prescribe a medication. Second, the subject can be entered into the system by hospital or office staff with a unique user name and personal password and as one of the doctor's patients. Third, the subject can log into the system from a computer or tablet in the hospital unit if receiving treatment as an inpatient, or in the doctor's office or at home if an outpatient, and can complete assessments of cognitive function to identify "localizer" cognitive impairments related to their CNS disorder. The identified cognitive impairments reflect the specific neural system that is dysfunctional. This is the target location for drug release. Fourth, the system can design, choose, and/or create a targeting activation task "game" that can activate the target neural system dysfunction to produce the localized change in pH, lactate level, blood flow, temperature, magnetic field, or concentration of the specific molecules to release the neurological drug at the physical locations of the neurofunctional system. Fifth, the subject can be instructed, and then reminded by the system, to play the cognitive game for a period of time, e.g., approximately 20-60 minutes, during a time interval after ingestion of the neurological drug appropriate for the pharmacokinetics of the ingested neurological drug. The goal is to wait long enough after ingestion to achieve near peak blood levels of the neurological drug. Sixth, this procedure can be repeated in relation to each dose of the neurological drug and for two times per day. Seventh, the system can repeat cognitive assessments regularly through the course of treatment to monitor improvement in the function of the target system and detect other impairments that need to be targeted. It may be common to identify more than one cognitive impairment "localizer", and include more than one targeting activation task "game" for targeted drug delivery.

Figure 7:
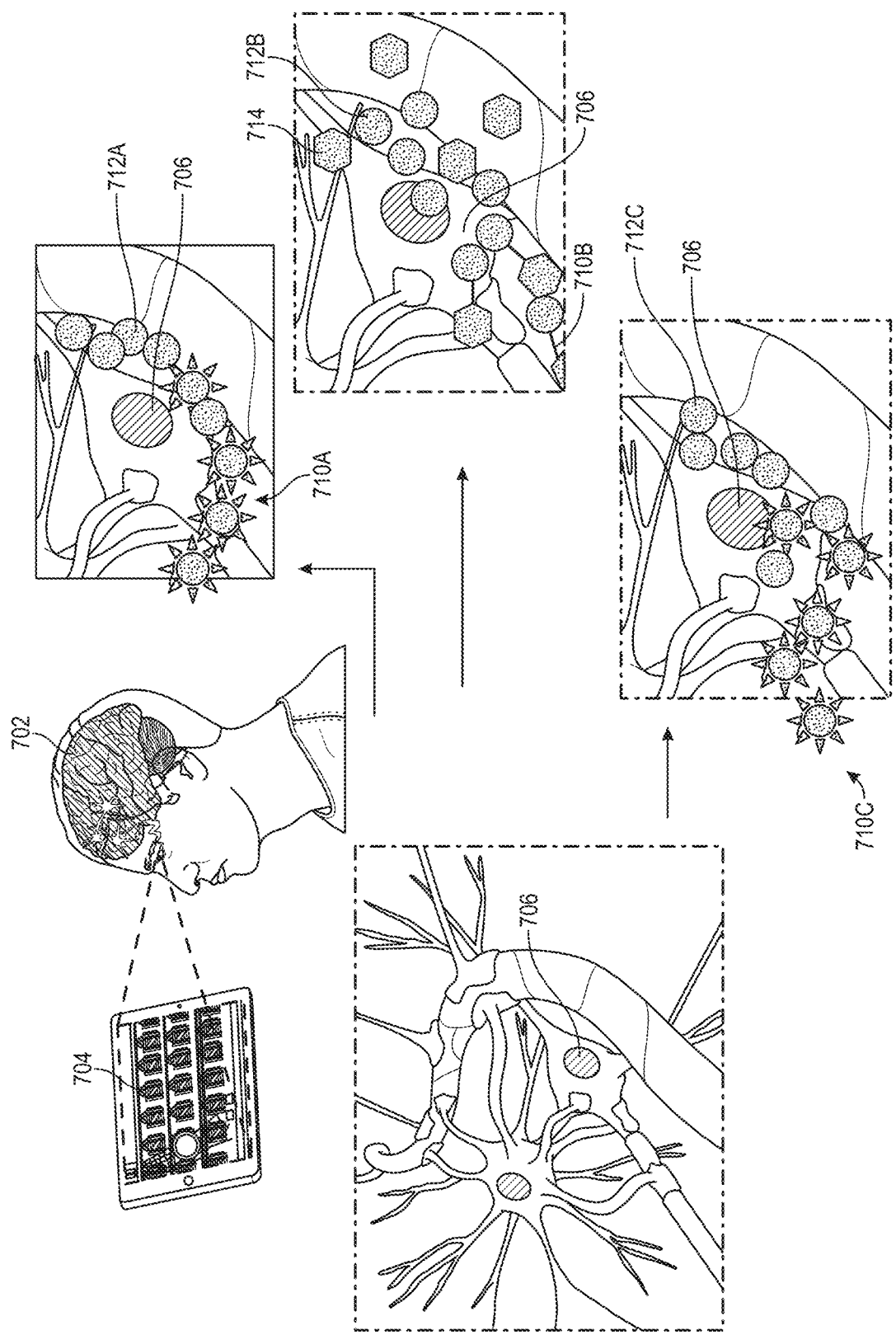
FIG. 7 illustrates effects in a brain of a subject performing a targeting activation task with a video display in accordance with an embodiment.

FIG. 7 illustrates effects in a brain of a subject 702 performing a targeting activation task 704 with a video display in accordance with an embodiment. The targeting activation task 704 can be a neurocognitive task or a sensory-motor brain activation task that is selected based on a determined dysfunction of a neurofunctional system of the subject 702. As illustrated in FIG. 7, the neurofunctional system can involve physical location 706, which corresponds to an area of the brain in which a neurological drug is to be released based on the dysfunction of the neurofunctional system for the subject 702.

As an example, a DDS 710A can be administered to the subject 702. The DDS 710A carries a neurological drug 712A and is configured to release the neurological drug 712A in response to an increased lactate release and a decreased pH level. The subject 702 can perform the targeting activation task 704 that results in increased neuronal firing at the physical location 706 in the brain, causing the increased lactate release and a decreased pH level at the physical location 706. Based on the increased lactate release and a decreased pH level at the physical location 706, the neurological drug 712A can be released from the DDS 710A. Thus, the neurological drug 712A is received by the physical location 706, but not other locations of the brain that do not experience increased neuronal firing as a result of the targeting activation task 704.

As another example, a DDS 710B can be administered to the subject 702. The DDS 710B includes a carrier 714 linked to a neurological drug 712B. The carrier 714 can be cleaved from the neurological drug 712B, thus resulting in activation of the neurological drug 712B, in response to an increased release of proteases. So, the subject 702 can perform the targeting activation task 704 that results in increased neuronal firing at the physical location 706, causing the release of proteases at the physical location 706. Based on the release of proteases at the physical location 706, the neurological drug 712B can be released from the DDS 710B. As a result, the neurological drug 712B is received by the physical location 706, but not other locations of the brain that do not experience increased neuronal firing as a result of the targeting activation task 704.

As yet another example, a DDS 710C can be administered to the subject 702. The DDS 710C carries a neurological drug 712C and is configured to release the neurological drug 712C in response to increased blood flow, decreased deoxyhemoglobin, and increased temperature. So, the subject 702 can perform the targeting activation task 704 that results in increased neuronal firing at the physical location 706, causing the increased blood flow, decreased deoxyhemoglobin, and increased temperature at the physical location 706. Based on the increased blood flow, decreased deoxyhemoglobin, and increased temperature at the physical location 706, the neurological drug 712C can be released from the DDS 710C. Thus, the neurological drug 712C is received by the physical location 706, but not other locations of the brain that do not experience increased neuronal firing as a result of the targeting activation task 704.

Figure 8:
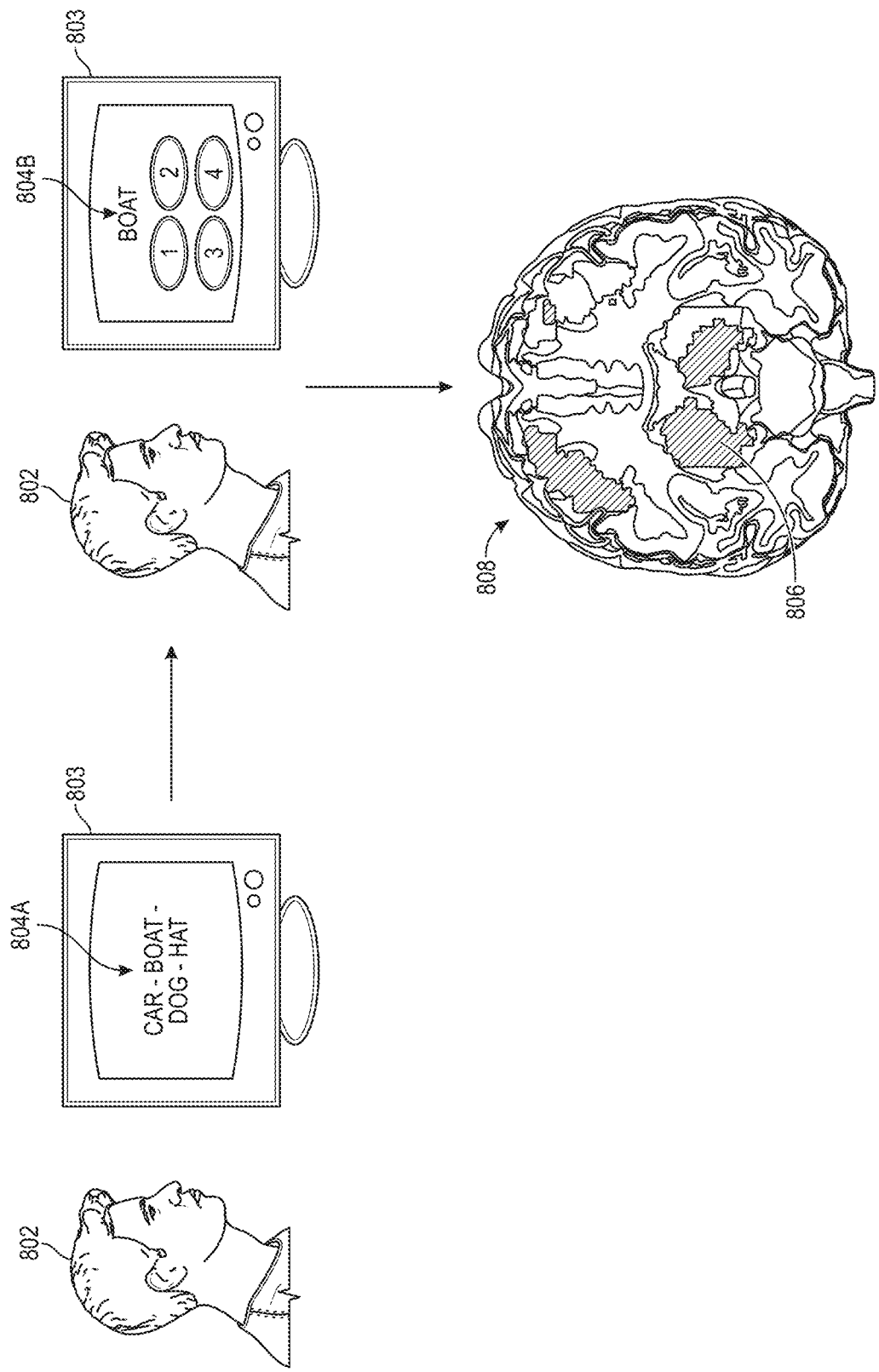
FIG. 8 illustrates an effect in a brain of a subject performing a targeting activation task in accordance with an embodiment.

FIG. 8 illustrates an effect in a brain 808 of a subject 802 performing a targeting activation task in accordance with an embodiment. The targeting activation task involves a video display 803 displaying an interactive game or a cognitive challenge. The subject 802 provides interactive inputs, which then cause an update to the video display 803. For example, if the subject 802 has schizophrenia, the targeting activation task can be a cognitive challenge designed to activate the associated striatum, where medication effect is needed for schizophrenia.

A first stage 804A of the targeting activation task is illustrated as involving the subject 802 being presented a series of words on the video display 803. After some time, a second stage 804B of the targeting activation task involves the subject 802 selecting a placement of one of the words in the series of words during the first stage 804A. For instance, if the word to locate is "boat," and the series of words in the first stage 804A is presented as "car-boat-dog-hat", then to correctly complete the targeting activation task, the subject 802 should select "2" during the second stage 804B. The number "2" is the position of the second word, "boat," in the series. The subject 802 can repeatedly be shown various series of words and select placements of words within the series. The targeting activation task can be sustained long enough to cause a desired change, e.g., a predetermined pH, lactate level, blood flow, temperature, magnetic field, or specific molecules released by brain cells, in a physical location 806 corresponding to the associated striatum of the brain 808 of the subject 802.

The targeting activation task may be adjusted over time based on a response of the subject 802 to the neurological drug or to improve specificity of where the neurological drug is released in response to the targeting activation response. For example, a sensor, such as a functional magnetic resonance imaging (fMRI) may be used to measure areas of brain activation during the targeting activation task and show that while the subject 802 performs the targeting activation task, another location of the brain 808, other than the physical location 806 desired for therapeutic drug release, is affected by the targeting activation task. As a result, the neurological drug is also released at the other location, which may not be desired. So, the targeting activation task may be adjusted in response to the fMRI. For example, if the physical location 806 is determined to be activated and experience the desired physiological change after the subject 802 performs the targeting activation task for one minute and the other location is determined to be activated and experience the desired physiological change after the subject 802 performs the targeting activation task for ten minutes, the length of the targeting activation task may be shortened to seven minutes so that the neurological drug is locally released at the physical location 806. Adjusting the targeting activation task may additionally or alternatively involve adjusting an intensity, e.g., speed, difficulty, etc., of the targeting activation task.

The measured releasing of the neurological drug may also be used to adapt the targeting activation task based on the changed pH, lactate level, blood flow, temperature, magnetic field, or concentration of the specific molecules in the brain 808 of the subject 802. For example, the targeting activation task may be adapted to more quickly display the first stage 804A and the second stage 804B for various series of words. The sensor can be used to continuously measure the degree of activation of the desired therapeutic target location, and once the sensor determines that a predetermined dose of the neurological drug is estimated to be released, the targeting activation task can be stopped.

Figure 9:
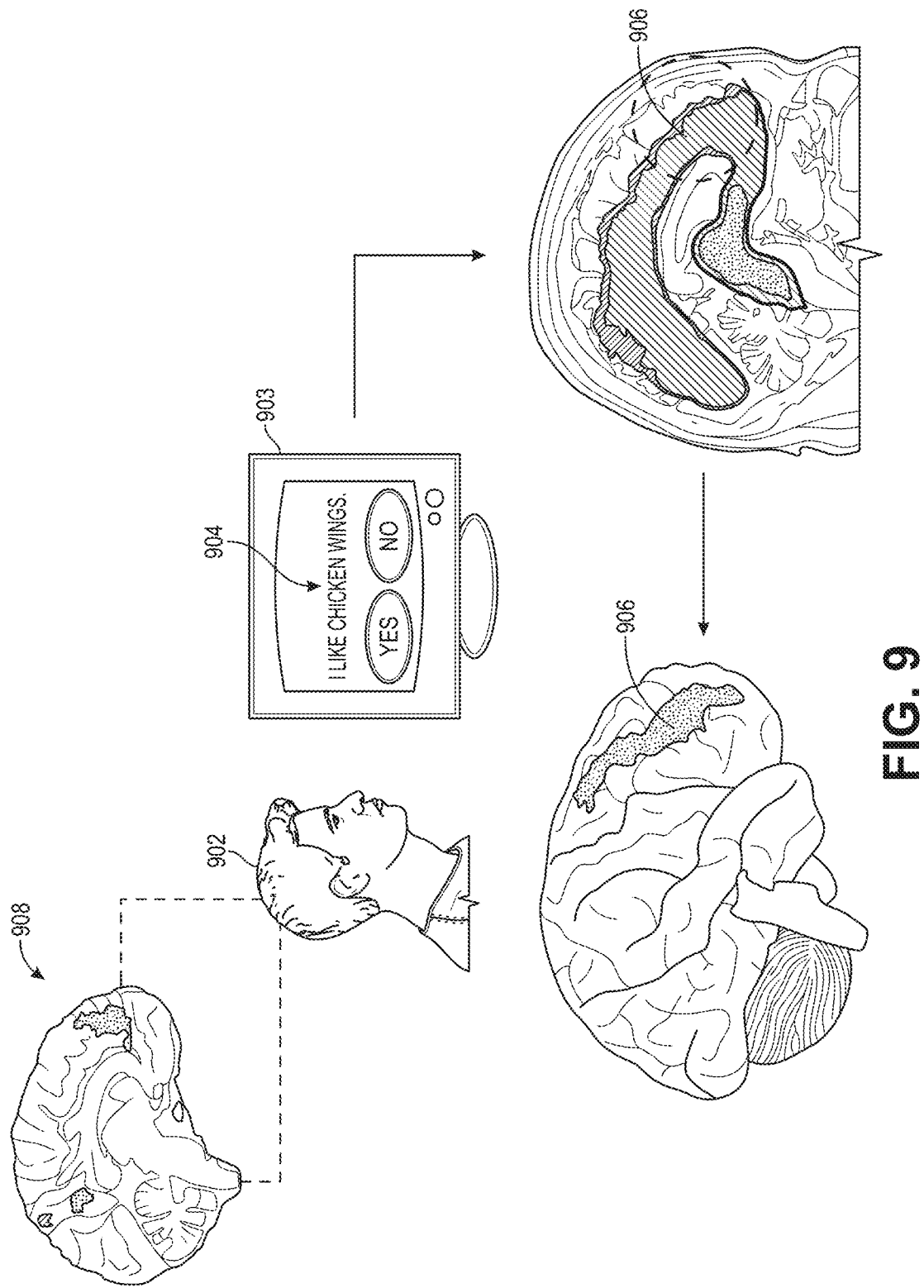
FIG. 9 illustrates an effect in a brain of a subject performing another targeting activation task in accordance with an embodiment.

FIG. 9 illustrates an effect in a brain 908 of a subject 902 performing another targeting activation task 904 in accordance with an embodiment. The targeting activation task 904 task involves a video display 903 displaying an interactive game or a cognitive challenge. The subject 902 provides interactive inputs, which then cause an update to the video display 903. For example, if the subject 902 has depression, the targeting activation task can be a cognitive challenge designed to activate the medial frontal gyrus of the brain 908, where medication effect is needed for depression.

The targeting activation task 904 is illustrated as involving the subject 902 being presented a statement on the video display 903. The subject 902 provides an input of a selection of "yes" or "no" indicating the subject's agreement with the statement. For instance, if the statement is "I like chicken wings", then the subject 902 selects "yes" to indicate their like of chicken wings or "no" to indicate their dislike of chicken wings. The subject 902 can repeatedly be shown various statements and select whether they agree or disagree with the statement. Since the frontal lobe, where the medial frontal gyrus is located, is associated with personality control, the subject 902 considering and responding to the statement can activate the medial frontal gyrus. The targeting activation task 904 can be sustained long enough to cause a desired change, e.g., a predetermined pH, lactate level, blood flow, temperature, magnetic field, or specific molecules released by brain cells, in a physical location 906 corresponding to the medial frontal gyrus of the brain 908 of the subject 902.

The targeting activation task may be adjusted over time based on a response of the subject 902 to the neurological drug as determined by improved function of the initially disease-disabled target region. This may, for example be in the form of measuring improved performance of the neurocognitive, sensory, or motor task used to determine the target for therapeutic drug release. Length, intensity, or other adjustment to the targeting activation task 904 may be made based on the measurement.

Figure 10:
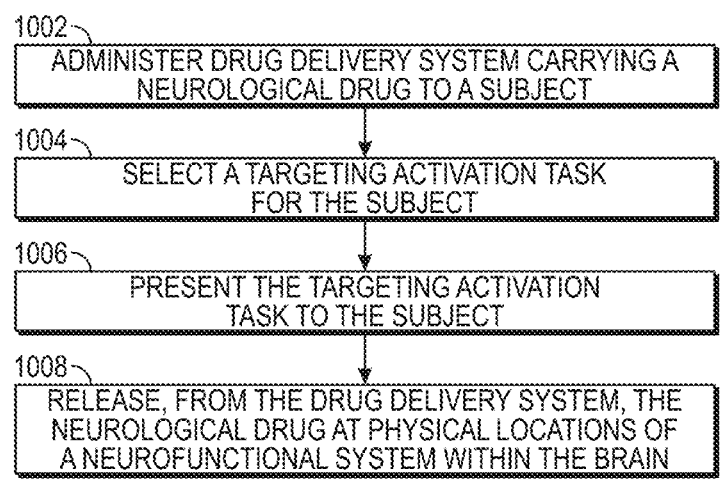
FIG. 10 illustrates a flowchart of a process for localized activation in the brain of neurological pharmacotherapy through tasks by a subject in accordance with an embodiment.

FIG. 10 illustrates a flowchart of a process for localized activation in the brain of neurological pharmacotherapy through tasks by a subject in accordance with an embodiment. In operation 1002, a DDS carrying a neurological drug is administered to a subject. The DDS can be selected from the group consisting of a DNA nanocage, cellular delivery system, a MEMs-based device, a polymer matrix, and a gene delivery system. The DDS is configured to release the neurological drug when encountering a predetermined pH, lactate level, blood flow, temperature, magnetic field, or specific molecules released by brain cells.

In operation 1004, a targeting activation task is selected for the subject. The targeting activation task is selected in order to change a pH, a lactate level, a blood flow, a temperature, a magnetic field, or a concentration of the specific molecules in physical locations of a predetermined neurofunctional system of a brain of the subject. The targeting activation task can include a neurocognitive task or a sensory-motor brain activation task. The neurocognitive task may involve an audible game or cognitive challenge or an interactive game or cognitive challenge. The sensory-motor brain activation task may involve the subject moving an appendage. The targeting activation task can be a task that activates the physical locations of the neurofunctional system. For example, a first targeting activation task can be selected if the neurofunctional system is associated with a striatum of the brain than if the neurofunctional system is associated with a medial frontal gyrus of the brain.

In operation 1006, the targeting activation task is presented to the subject. Presenting the targeting activation task can involve displaying the interactive game or cognitive challenge on a video display, which may include virtual reality goggles. Presenting the targeting activation task may additionally or alternatively involve playing the audible game or cognitive challenge on a speaker. A predetermined time may be waited before presenting the targeting activation task to allow for the drug delivery system to cross the blood brain barrier of the subject.

In operation 1008, the neurological drug is released from the DDS at physical locations of a neurofunctional system within the brain of the subject. Depending on the DDS, releasing of the neurological drug may involve unbinding from or exposing an active region of the neurological drug. The neurological drug is released based on the physical locations of the changed pH, lactate level, blood flow, temperature, magnetic field, or concentration of the specific molecules caused by the targeting activation task. That is, since the targeting activation task causes a predetermined physiological change in physical locations associated with the neurofunctional system, the neurological drug is released at the physical locations rather than throughout a whole brain of the subject, thereby reducing potential side effects of the neurological drug.

Experimental Method in Prototype

Methods can be tested and refined initially in cell cultures and then with mice.

Mouse neuronal cells can be cultured on 60-channel 8×8 microelectrode arrays (MEAs). Experimental procedures can follow those in which a selected network of cultured cells within the MEA is "trained" to promote growth of synaptic connections and enhanced trans-synaptic response to probe stimulation. It has been demonstrated that such trained systems are sensitive to inhibition of synaptic transmission by application of pharmacologic agents to culture medium. One can use the system to demonstrate pH-dependent local release from the DDS of a drug that decreases synaptic transmission and neuronal firing, for example the N-methyl-D-aspartate (NMDA) antagonist ketamine. One can compare release by three variations of the DDS that differ in pH sensitivity release set points. Local changes in pH associated with trans synaptic transmission and neuronal activity can also be measured.

In one experiment, ten MEAs can be created for each of the experimental conditions. Signals for spike detection can be recorded from each electrode at a rate of 25 kHz with bandpass filter from 300 Hz to 3 kHz. Thresholds for spike detection can be set individually for each recording electrode at 5 times the standard deviation of the base noise level over 500 ms. A subset of electrode stimulation sites in an "L" configuration can be used to provide probe stimuli to evaluate neuronal responsiveness before and after presentation of training stimulation through the same electrodes. The probe pulse can include 0.5 Hz biphasic pulse, 200 microsec pulse duration with 900 mV amplitude. The training pulse can include 40 pulse trains each containing 100 biphasic pulses with a 4 msec inter-pulse period, a 200 microsec pulse duration and a 900 mV amplitude. Spike frequency can be counted in the 50 ms following stimulus pulses, divided into 10 ms bins, in the following conditions (10 MEAs/condition):
i. Control MEAs with no training and no drug
ii. Trained MEAs with no drug
iii. Trained MEAs with DDS without drug
iv. Trained MEAs with DDS+ketamine, but DDS pH release sensitivity set well beyond expected range
v. Trained MEAs with drug ketamine
vi. Trained MEAs with DDS+ketamine, with low DDS pH release sensitivity
vii. Trained MEAs with DDS+ketamine, with mid DDS pH release sensitivity
viii. Trained MEAs with DDS+ketamine, with high DDS pH release sensitivity Conditions ii-iv can show higher spike counts than condition i, but without difference among them. The difference between ii and i can demonstrate the validity of the training paradigm. The similarity of conditions ii, iii, and iv can demonstrate that the DDS alone or with unreleased ketamine are inactive. Condition v, and conditions vi and/or vii and/or viii can show lower spike counts than condition ii. This shows that the DDS successfully released drug at one or more of the pH release sensitivities.

Differences among conditions vi, vii, and viii provide information important to balancing specificity and sensitivity of the DDS release.

Test and Refine in Mice

In vivo experiments in mice can be done to demonstrate both effectiveness and specificity of localized drug release triggered by localized neuronal activity associated with auditory or visual sensory stimulation. They may not limit the use of simple auditory or visual stimulation to trigger localized release of medication, but perhaps only to establish a prototype. Neurosystems involved in cognitive processing, or other brain functions, can also be activated to induce local release of medication. In these experiments, cell firing and local pH can be measured from auditory and visual cortex while the animals receive either auditory or visual stimulation. They can be designed to show DDS drug release associated with pH change in auditory cortex and not visual cortex with auditory stimulation and the reverse with visual stimulation. pH can be measured with single cell resolution using a surface-enhanced Raman scattering (SERS) optophysiological probe or another suitable method.

Several well-established methods exist for measuring single neuron spike trains and small network activation in mice, each also providing different types of additional information of potential added value. One, for example, combines patch-clamp recording using commercially available recording systems to measure spontaneous and induced spike trains from individual neurons and also does ribonucleic acid (RNA)-based subtyping of the individual neurons. Another uses a wireless miniature fluorescence microscope capable of recording neuronal activity with single cell resolution in free-moving mice.

Effects of synaptic agonists and/or antagonists delivered by pH-sensitive DDSs to auditory or visual neural processing systems activated by sensory stimulation can be measured in groups of 5-10 mice. Neuronal activity can be measured in auditory and visual processing areas before and after auditory or visual stimulation under five pharmacologic conditions: placebo, free drug, drug in 3 DDSs with one to three differing in pH release set points. Sensory stimulation protocols for eliciting neural activity in auditory and visual cortexes in mice are well established. One can use pulsed noise trains and pulsed visual stimuli to increase extracellular lactate and alter extracellular pH.

Although specific embodiments of the invention have been described, various modifications, alterations, alternative constructions, and equivalents are also encompassed within the scope of the invention. Embodiments of the present invention are not restricted to operation within certain specific environments, but are free to operate within a plurality of environments. Additionally, although method embodiments of the present invention have been described using a particular series of and steps, it should be apparent to those skilled in the art that the scope of the present invention is not limited to the described series of transactions and steps.

Further, while embodiments of the present invention have been described using a particular combination of hardware, it should be recognized that other combinations of hardware are also within the scope of the present invention.

The specification and drawings are, accordingly, to be regarded in an illustrative rather than a restrictive sense. It will, however, be evident that additions, subtractions, deletions, and other modifications and changes may be made thereunto without departing from the broader spirit and scope.

What is claimed is:

1. A method for localized activation in the brain of neurological pharmacotherapy through tasks by a subject, the method comprising:
administering a drug delivery system (DDS) to a subject, the DDS carrying a neurological drug, the drug delivery system configured to release the neurological drug when encountering a predetermined pH, lactate level, blood flow, temperature, magnetic field, or specific molecules released by brain cells;
selecting a targeting activation task for the subject, the targeting activation task including a neurocognitive task or a sensory-motor brain activation task;
presenting the targeting activation task to the subject, wherein the targeting activation task is selected in order to change a pH, a lactate level, a blood flow, a temperature, a magnetic field, or a concentration of the specific molecules in physical locations of a predetermined neurofunctional system of a brain of the subject; and releasing, from the DDS, the neurological drug at the physical locations of the neurofunctional system within the brain based on the physical locations of the changed pH, lactate level, blood flow, temperature, magnetic field, or concentration of the specific molecules caused by the targeting activation task.

2. The method of claim 1 wherein the targeting activation task is a sensory-motor brain activation task, and presenting of the targeting activation task includes:
instructing the subject to move an appendage.

3. The method of claim 2 wherein the movement includes periodic movement in a rhythm.

4. The method of claim 2 wherein the instructing includes starting or stopping the movement.

5. The method of claim 1 wherein the targeting activation task is a neurocognitive task, and presenting of the targeting activation task includes:
displaying, on a video display, an interactive game or cognitive challenge;
receiving interactive inputs from the subject; and
updating the video display in response to the interactive inputs.

6. The method of claim 5 wherein the video display comprises virtual reality goggles.

7. The method of claim 1 wherein the targeting activation task is a neurocognitive task, and presenting of the targeting activation task includes:
playing, on a speaker, an audible game or cognitive challenge; and
receiving interactive inputs from the subject,
wherein the audible game or cognitive challenge is updated in response to the interactive inputs.

8. The method of claim 1 further comprising:
measuring the releasing through a sensor; and
adjusting a length or intensity of the targeting activation task in response to a value obtained from the measuring.

9. The method of claim 8 further comprising:
adapting the targeting activation task based on the changed pH, lactate level, blood flow, temperature, magnetic field, or concentration of the specific molecules in the brain of the subject; and
stopping the targeting activation task when a predetermined dose of the neurological drug is estimated to be released.

10. The method of claim 1 further comprising:
waiting a predetermined time for the drug delivery system to cross a blood brain barrier of the subject before presenting the targeting activation task.

11. The method of claim 1 wherein the drug delivery system is selected from the group consisting of a deoxyribonucleic acid (DNA) nanocage, cellular delivery system, a microelectromechanical (MEMs)-based device, a polymer matrix, and a gene delivery system.

12. The method of claim 1 wherein the releasing of the neurological drug includes unbinding from or exposing an active region of the neurological drug.

13. The method of claim 1 wherein the subject is a human.

14. The method of claim 13 wherein the human suffers from a central nervous system disease.

15. The method of claim 14 wherein the central nervous system disease is a psychiatric disease.

* * * * *

UNITED STATES PATENT AND TRADEMARK OFFICE
CERTIFICATE OF CORRECTION

| | |
|---|---|
| PATENT NO. | : 11,491,276 B2 |
| APPLICATION NO. | : 17/687263 |
| DATED | : November 8, 2022 |
| INVENTOR(S) | : Bruce E. Wexler |

It is certified that error appears in the above-identified patent and that said Letters Patent is hereby corrected as shown below:

In the Specification

In Column 2, Line 62, delete "Hi" and insert -- $H_1$ --.

In Column 3, Line 6, delete "Hi" and insert -- $H_1$ --.

In Column 7, Line 52, delete "poly(allyamine" and insert -- poly(allylamine --.

Signed and Sealed this
Sixteenth Day of May, 2023

Katherine Kelly Vidal
*Director of the United States Patent and Trademark Office*